United States Patent
Cunningham et al.

(10) Patent No.: US 9,949,477 B2
(45) Date of Patent: *Apr. 24, 2018

(54) DURABLE ANTIMICROBIAL COMPOSITION

(75) Inventors: Corey T. Cunningham, Larsen, WI (US); Rebecca Ann Vongsa, Oshkosh, WI (US); Stacy A. Mundschau, Weyauwega, WI (US); David W. Koenig, Menasha, WI (US); Douglas R. Hoffman, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 584 days.

This patent is subject to a terminal disclaimer.

(21) Appl. No.: 12/982,058

(22) Filed: Dec. 30, 2010

(65) Prior Publication Data

US 2012/0171155 A1 Jul. 5, 2012

(51) Int. Cl.
*A01N 33/12* (2006.01)
*A01N 37/36* (2006.01)
*A01N 59/00* (2006.01)

(52) U.S. Cl.
CPC ............ *A01N 33/12* (2013.01); *A01N 37/36* (2013.01); *A01N 59/00* (2013.01)

(58) Field of Classification Search
CPC combination set(s) only.
See application file for complete search history.

(56) References Cited

U.S. PATENT DOCUMENTS

| | | | |
|---|---|---|---|
| 3,775,332 A | 11/1973 | Heins et al. | |
| 4,075,116 A | 2/1978 | Mesaros | |
| 4,316,879 A | 2/1982 | Pinsky et al. | |
| 4,687,663 A | 8/1987 | Schaeffer | |
| 4,812,308 A | 3/1989 | Winston et al. | |
| 5,015,408 A | 5/1991 | Reuss | |
| 5,061,485 A | 10/1991 | Oakes et al. | |
| 5,102,575 A | 4/1992 | Lanniel et al. | |
| 5,357,636 A * | 10/1994 | Dresdner et al. | 2/161.7 |
| 5,438,034 A | 8/1995 | Walker | |
| 5,851,420 A | 12/1998 | Kim et al. | |
| 5,861,365 A | 1/1999 | Colurciello, Jr. et al. | |
| 5,965,110 A | 10/1999 | Arnold | |
| 6,248,707 B1 | 6/2001 | Doetsch et al. | |
| 6,270,754 B1 | 8/2001 | Zhou et al. | |
| 6,274,540 B1 | 8/2001 | Scheibel et al. | |
| 6,613,728 B1 | 9/2003 | Sirianni et al. | |
| 6,841,090 B1 | 1/2005 | Serego Allighieri et al. | |
| 7,598,214 B2 | 10/2009 | Cusack et al. | |
| 2002/0031966 A1 | 3/2002 | Tomarchio et al. | |
| 2002/0040092 A1 | 4/2002 | Siddiqui et al. | |
| 2002/0110483 A1 | 8/2002 | Aamodt et al. | |
| 2002/0177541 A1 | 11/2002 | Tarara et al. | |
| 2003/0180229 A1 | 9/2003 | Kosti | |
| 2004/0224872 A1 | 11/2004 | Fine et al. | |
| 2005/0020466 A1 | 1/2005 | Man et al. | |
| 2006/0003649 A1 | 1/2006 | Runge et al. | |
| 2007/0027119 A1 | 2/2007 | Ahmed et al. | |
| 2007/0065475 A1 | 3/2007 | Elfersy | |
| 2007/0129474 A1 | 6/2007 | Salamone et al. | |
| 2007/0184013 A1 * | 8/2007 | Snyder et al. | 424/78.3 |
| 2007/0202059 A1 | 8/2007 | Longo et al. | |
| 2008/0076313 A1 | 3/2008 | Uitenbroek et al. | |
| 2008/0145664 A1 | 6/2008 | Sirovatka et al. | |
| 2008/0175919 A1 | 7/2008 | Mohammadi et al. | |
| 2008/0206293 A1 | 8/2008 | Toreki et al. | |
| 2008/0286223 A1 | 11/2008 | Fuls et al. | |
| 2009/0004287 A1 * | 1/2009 | Kimler et al. | 424/616 |
| 2009/0041820 A1 | 2/2009 | Wu et al. | |
| 2009/0104281 A1 | 4/2009 | Taylor et al. | |
| 2009/0155327 A1 | 6/2009 | Martin et al. | |
| 2009/0196939 A1 | 8/2009 | Hei et al. | |
| 2009/0226541 A1 * | 9/2009 | Scholz et al. | 424/672 |
| 2010/0240799 A1 * | 9/2010 | Hofmann et al. | 523/122 |

FOREIGN PATENT DOCUMENTS

| | | |
|---|---|---|
| DE | 27 41 072 A1 | 3/1979 |
| GB | 797701 A | 7/1958 |
| GB | 1 126 953 A | 9/1968 |
| JP | 57-046973 A | 3/1982 |
| WO | WO 1994/003283 A1 | 2/1994 |
| WO | WO 1996/006910 A2 | 3/1996 |
| WO | WO 1997/030586 A1 | 8/1997 |
| WO | WO 1998/054279 A1 | 12/1998 |
| WO | WO 2001/028339 A2 | 4/2001 |
| WO | WO 2002/003799 A2 | 1/2002 |
| WO | WO 2003/061610 A1 | 7/2003 |
| WO | WO 2006/138111 A1 | 12/2006 |
| WO | WO 2007/002478 A2 | 1/2007 |
| WO | WO 2007/027859 A1 | 3/2007 |

\* cited by examiner

*Primary Examiner* — Robert S Cabral
(74) *Attorney, Agent, or Firm* — Kimberly-Clark Worldwide, Inc.

(57) ABSTRACT

The present invention relates to compositions having durable antimicrobial activity. The compositions include a carbonate/bicarbonate salt of a quaternary ammonium cation, an organic acid, hydrogen peroxide and a polymer. The polymer is selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, poly(t-butyl acrylate co-ethyl acrylate co-methacrylic acid), polyethylene oxide, polyquaternium-16, polyquaternium-22, polyquaternium-67 and mixtures thereof.

15 Claims, No Drawings

DURABLE ANTIMICROBIAL COMPOSITION

FIELD OF THE INVENTION

The present invention relates to compositions having durable antibacterial activity. The compositions include a carbonate/bicarbonate salt of a quaternary ammonium cation, an organic acid, hydrogen peroxide and a polymer. The polymer is selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, poly(t-butyl acrylate co-ethyl acrylate co-methacrylic acid), polyethylene oxide, polyquaternium-16, polyquaternium-22, polyquaternium-67 and mixtures of these polymers.

BACKGROUND OF THE INVENTION

In order to protect health and maintain hygiene, a variety of environments require controlled and limited microbial growth. Such environments include temporary and permanent healthcare facilities, caregiver facilities (e.g. daycares, nursing homes, etc.) and households. When growth of potentially harmful microbes is not controlled/limited in these environments, the risk of infection and spread of disease increases. Infection and disease may compromise the health and safety of humans and/or animals occupying these environments. While potentially not as sensitive as the above-identified environments, workplace and public environments may also be negatively impacted by uncontrolled/unlimited growth of disease-causing microbes.

Some types of microorganisms (bacteria, viruses, fungi, etc.) are capable of negatively impacting the health and/or safety of living organisms. Such microorganisms can be transmitted by contact with surfaces on which the microorganisms are present and/or multiplying and by contact between humans/animals already infected with particular microorganisms. When such microorganisms spread and infect new "hosts", the "host" can either go from an otherwise healthy state to a state of illness or from a "compromised" state (i.e. a state of pre-existing illness or a weak immune system) to a more serious/severe state. The public health impact of the undesired spread of microorganisms is significant as reflected by time out of school, time away from work (either for self or to care for others not able to care for themselves), additional time for which professional health care is needed, etc. Therefore, it is desirable to be able to prevent or inhibit microbial presence/growth on targeted surfaces. The presence of microorganisms can be eliminated/controlled using surface treatments that may be applied directly (as from a spray bottle) and by using wipes or other carriers that include the surface treatment. Further, it is desirable that such surface treatments have durability and persistence so that they do not need to be re-applied on a frequent basis.

There are many detergent, disinfectant, cleaning and antimicrobial compositions known in the art for killing and preventing growth of microorganisms. Those compositions include components/ingredients that are well-known for antimicrobial functionality. For example, quaternary ammonium compounds are considered "broad spectrum" antimicrobial cationic compounds that are effective against both Gram positive (e.g. *Staphylococcus* species) and Gram negative (e.g. *Escherichia coli*) microorganisms. Other components/ingredients that may be incorporated into products for removing/reducing microorganisms on surfaces include alcohols, acids and bleaching agents, such as hydrogen peroxide. Not all of the antimicrobial components can be used at the same time because some of them form unstable combinations.

Disinfecting and cleaning compositions that provide antimicrobial activity over a period of time are also known in the art. For example, U.S. Pat. No. 6,270,754 issued to Zhou et al. and entitled "Antimicrobial Cleaning Composition" (hereinafter "the '754 patent") is directed to an antibacterial cleaning composition that exhibits germicidal activity for sustained periods of time. The '754 patent discloses an aqueous cleaning composition that includes a quaternary ammonium compound, an anionic polymer (where the anionic polymer has an acid number greater than 10 and the anionic polymer is partially or completely neutralized by the quaternary ammonium compound to form a polymer complex), a dispersing agent and/or a water-miscible solvent. The aqueous cleaning composition of the '754 patent has antibacterial activity against both Gram positive and Gram negative bacteria. However, the components of the '754 patent may not be effective against a broader range of microorganisms, such as non-enveloped viruses.

In addition to the composition of the '754 patent, there are compositions known in the art that are effective against a broad spectrum of microorganisms and continue to have activity for a period of time. For example, U.S. Pat. No. 7,598,214 issued to Cusack et al. and entitled "Disinfecting Compositions Containing A Polymer Complex Of an Organic Acid" (hereinafter "the '214 patent") is directed to compositions that include at least one organic acid and at least one polymer capable of forming a complex with the at least one organic acid. The compositions of the '214 patent may also optionally include an anionic surfactant and an organic solvent. The organic acid may be citric acid and examples of suitable polymers include vinylpyrrolidone/dimethylaminoethylmethacrylate copolymer, vinylpyrrolidone/vinylacetate copolymers, vinylpyrrolidone/vinylcaprolactum/ammonium derivative terpolymers and polyvinylpyrrolidone. The compositions of the '214 patent need an organic solvent and they are pH sensitive. Because of the acid-based reaction between the polymer having a tertiary amine functionality and the organic acid, the compositions are not effective in higher pH environments. In a higher pH environment, the reaction would reverse and the polymer would be rendered ineffective because it would be neutral. Though the compositions of the '214 patent are effective against a broader spectrum of microorganisms, the compositions may not be effective against the spore-form of all microorganisms because the compositions cannot penetrate through the outer wall of the spores.

While many antimicrobial compositions are known and while some of those compositions maintain their antimicrobial activity over a period of time, there remains a need in the art for a durable antimicrobial composition that is effective against a broad range of microorganisms, including the spore-form of potentially harmful microorganisms. Additionally, there remains a need for a durable antimicrobial composition that is stable (i.e. is not reactive) so that it is not unnecessarily harsh (causing wear or corrosion) on the surfaces on which it is used. Further, there remains a need for a durable antimicrobial composition that does not require a volatile solvent that may have an unpleasant smell.

SUMMARY OF THE INVENTION

The present invention relates to durable antimicrobial compositions that are effective against a broad range of potentially harmful microorganisms and that do not have to be reapplied on a frequent basis to the surfaces on which controlled microbial growth is desired. The compositions of the invention are effective against a broad range of microorganisms, including the spore-form of microorganisms, because of the composition components, which are unexpectedly stable in combination with each other. Additionally, the compositions of the invention do not need to contain a volatile solvent that could make the compositions unpleasant to use.

In one aspect, the compositions of the invention have durable antimicrobial activity and include a carbonate/bicarbonate salt of a quaternary ammonium cation, an organic acid, hydrogen peroxide and a polymer. The polymer is selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, poly(t-butyl acrylate co-ethyl acrylate co-methacrylic acid), polyethylene oxide, polyquaternium-16, polyquaternium-22, polyquaternium-67 and mixtures of such polymers. As described herein, the compositions have a durable or persistent activity to kill and prevent the growth of potentially harmful microorganisms. The durability of the compositions is indicated by the compositions retaining antimicrobial activity after twenty-five insults of $E.$ $coli$ organisms as measured by a log 2 reduction in organisms upon the twenty-fifth insult of $10^6$ total organisms. The compositions of the invention are stable; the stability of the compositions is reflected by the compositions maintaining their efficacy during shelf-life studies. For example, the compositions remain effective (meaning, they have the same level of durability to effect a log 2 reduction in organisms after twenty-five insults of $10^6$ organisms) after storage for three months at 40° C.; further, the compositions remain effective after storage for one month at 50° C., nine months at 25° C. and after three freeze-thaw cycles. The compositions are liquid at room temperature and can be applied directly to a surface for which it is desired to prevent or inhibit microbial growth. The compositions may be applied using a spray bottle or other known structure for dispensing liquids. Alternatively, the compositions may be applied to a surface by transfer from a basesheet, such as a wiper, into which a representative composition has been incorporated. The basesheet may be made of a nonwoven material or of a cellulosic material. More particularly, the composition may include from 0.2% by weight to 15.0% by weight of the carbonate/bicarbonate salt of a quaternary ammonium cation. The composition may include from 0.1% by weight to 3.0% by weight of the organic acid, which may be selected from citric, malic, maleic, oxalic, glutaric, succinic, lactic, glycolic, fumaric, acetic, benzoic, propionic, sorbic, tartaric, formic and mixtures of such organic acids. The composition may include from 0.5% by weight to 5.0% by weight of hydrogen peroxide and the composition may include from 0.5% by weight to 10% by weight of polymer.

In another aspect, the present invention relates to a method of inhibiting the growth of microorganisms on a surface and of providing sustained antimicrobial activity on a surface. The method may be practiced to inhibit the growth of targeted microorganisms or to indiscriminately inhibit the growth of microorganisms. The surface may be any material capable of supporting the growth of microorganisms. The surface may be part of a relatively durable object or part of a disposable object. The surface may be hard, such as a countertop, tabletop, doorknob, telephone, keyboard or light switch; alternatively, the surface may be soft, such as a fabric surface (e.g. curtains, pillows, upholstery, bedspreads, etc.). The method includes a step of providing a composition; the composition includes a carbonate/bicarbonate salt of a quaternary ammonium cation, an organic acid, hydrogen peroxide and a polymer. The polymer is selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, poly(t-butyl acrylate co-ethyl acrylate co-methacrylic acid), polyethylene oxide, polyquaternium-16, polyquaternium-22, polyquaternium-67 and mixtures thereof. The method also includes a step of applying the composition to the surface in an amount to substantially cover the surface. Further, the method includes a step of re-applying the composition to the surface after 48 hours. The composition is re-applied after 48 hours to maintain the desired antimicrobial activity. Alternatively, the composition may be re-applied to the surface after 24 hours. The antimicrobial activity is indicated by antimicrobial activity persisting after twenty-five insults of $E.$ $coli$ as measured by a log 2 reduction in organisms upon the twenty-fifth insult of $10^6$ total organisms.

These aspects and additional aspects of the invention will be described in greater detail herein. Further, it is to be understood that both the foregoing general description and the following detailed description are exemplary and are intended to provide further explanation of the invention claimed.

DETAILED DESCRIPTION OF THE INVENTION

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The present invention relates to compositions having durable antimicrobial activity. The compositions may be used to kill or to inhibit the growth of microorganisms that are potentially harmful or capable of causing disease. The compositions of the invention do not need to contain a volatile solvent and therefore, do not generate an unpleasant smell when used. The compositions are effective at killing and/or inhibiting growth of a broad range of microorganisms. For example, the compositions are effective against both Gram positive and Gram negative bacteria. Additionally, the compositions are effective against viruses, fungi, mildew and mold. Further, the compositions are effective against bacteria that form spores, bacteria with waxy outer layers, fungi that form spores (fungal spores) and enveloped and non-enveloped viruses. Without wishing to be bound by theory, it is believed that the composition is capable of breaking down the waxy outer layer of a bacteria or outer layer of a spore so that the composition can penetrate into the microorganism beyond the outer layer.

The compositions of the invention may be used to control microbial growth on a variety of surfaces, including relatively durable objects having both hard and soft surfaces; for example, appropriate surfaces may include door knobs, light switches, countertops, sinks, wash basins, telephones, keyboards, remote controls, medical instruments, upholstery, curtains, bedspreads, towels and shoes. The compositions may be applied to the targeted surface either directly, in liquid form, such as by a spray bottle or similar packaging capable of delivering a liquid composition in a relatively uniform amount over the full surface to be covered. Alternatively, the compositions may be applied to the targeted surface by a carrier, such as a basesheet (i.e. a "wet" wipe or wiper). Because the compositions are liquid at room temperature, the composition may be applied to a surface by wiping the surface with a basesheet that has been saturated with the composition; the composition will transfer from the basesheet to the surface. The basesheet may be formed from one or more woven materials, nonwoven materials, cellulosic materials and combinations of such materials. More specifically, the basesheet may be formed of nonwoven fibrous sheet materials that include meltblown, spunlace, coform, air-laid, bonded-carded web materials, hydroentangled materials and combinations of such materials. Such materials can be made of synthetic or natural fibers or a combination of such fibers. Typically, the basesheet will have a basis weight of from 25 grams per square meter to 120 grams per square meter and desirably from 40 grams per square meter to 90 grams per square meter.

The basesheet may be constructed of a coform material of polymer fibers and absorbent fibers having a basis weight of from 45 to 80 grams per square meter and desirably 60 grams per square meter. Typically, such coform basesheets are constructed of a gas-formed matrix of thermoplastic polymeric meltblown fibers and cellulosic fibers. Various suitable materials may be used to provide the polymeric meltblown fibers, such as, for example, polypropylene microfibers. Alternatively, the polymeric meltblown fibers may be elastomeric polymer fibers, such as those provided by a polymer resin. For instance, VISTAMAXX elastic olefin copolymer resin designated PLTD-1810, available from ExxonMobil Corporation of Houston, Tex., or KRATON G-2755, available from Kraton Polymers of Houston, Tex., may be used to provide stretchable polymeric meltblown fibers for the coform basesheets. Other suitable polymeric materials or combinations thereof may alternatively be utilized as known in the art.

The coform basesheet additionally may be constructed of various absorbent cellulosic fibers, such as, for example, wood pulp fibers. Suitable commercially available cellulosic fibers for use in the coform basesheets can include, for example, NF 405, which is a chemically treated bleached southern softwood Kraft pulp, available from Weyerhaeuser Co. of Washington, D.C.; NB 416, which is a bleached southern softwood Kraft pulp, available from Weyerhaeuser Co.; CR-0056, which is a fully debonded softwood pulp, available from Bowater, Inc. of Greenville, S.C.; Golden Isles 4822 debonded softwood pulp, available from Koch Cellulose of Brunswick, Ga.; and SULPHATATE HJ, which is a chemically modified hardwood pulp, available from Rayonier, Inc. of Jessup, Ga. The relative percentages of the polymeric meltblown fibers and cellulosic fibers in the coform basesheet may vary over a wide range depending upon the desired characteristics of the wipes. For example, the coform basesheet may have from 10 weight percent to 90 weight percent, desirably from 20 weight percent to 60 weight percent, and more desirably from 25 weight percent to 35 weight percent of polymeric meltblown fibers based on the dry weight of the coform basesheet.

The compositions of the invention may be incorporated into the basesheet in an add-on amount of from 50% (by weight of the basesheet) to 800% (by weight of the basesheet). More specifically, the compositions may be incorporated into the basesheet in an add-on amount of from 200% (by weight of the basesheet) to 600% (by weight of the basesheet) or from 400% (by weight of the basesheet) to 600% (by weight of the basesheet). The composition add-on amounts may vary depending on the composition of the basesheet.

The present invention relates to compositions having durable antimicrobial activity. The "durability" or "persistence" of antimicrobial activity is descriptive of a benefit provided by the compositions of the invention. From a cost and efficiency standpoint, it is desirable to maintain antimicrobial activity on a surface over a period of time with one application of a composition rather than having to frequently apply a composition because its antimicrobial activity rapidly dissipates. From a public health standpoint, a durable antimicrobial composition is desirable because such a composition is more likely to prevent microbial growth than a composition that is weaker to begin with and a durable antimicrobial composition introduces less liquid/material into the environment, thereby decreasing the opportunity for microbes to develop resistance. The durability of the compositions of the invention is measured by activity after twenty-five (25) insults with a representative Gram negative bacterium, Escherichia coli (E. coli). The compositions of the invention retain activity sufficient to cause a log 2 reduction upon the twenty-fifth insult of $10^6$ total E. coli organisms. Additionally, the durability of the compositions of the invention is measured by ability to effect >log 2 reduction against Gram positive bacteria, Gram negative bacteria, enveloped viruses, non-enveloped viruses, fungi, mildew and mold twenty-four (24) hours after application of the composition to a surface. Further, the durability of the compositions of the invention is measured by ability to effect >log 2 reduction in microorganisms in the presence of soil after either of the first two assays described above (i.e. (1) $25^{th}$ insult of $10^6$ total organisms; or (2) twenty-four hours after application). From a practical standpoint, a standard surface, such as a countertop, table, telephone, etc., in a susceptible environment, such as a hospital or daycare facility, is continuously exposed to potentially harmful microorganisms. Given the rate at which exposure to new microorganisms typically occurs, a durable antimicrobial composition may be applied to the surface in a timeframe of every 24 hours to 48 hours in order to kill and/or to prevent the growth of microorganisms. Comparatively, an antimicrobial composition that is not durable would need to be applied continuously to a surface to maintain a comparable level of antimicrobial activity. In a less susceptible environment and with a less susceptible surface, such as draperies in a home, the durable antimicrobial composition may last up to seven days at full activity.

The compositions of the invention include a carbonate/bicarbonate salt of a quaternary ammonium cation. Quaternary ammonium compounds are generally considered "broad spectrum" antimicrobial cationic compounds that have efficacy against both Gram positive and Gram negative microorganisms. The carbonate/bicarbonate salts of quaternary ammonium cations may be selected from dioctyldimethylammonium carbonate, decyloctyldimethylammonium carbonate, didecyldimethylammonium carbonate, benzalkonium carbonate, benzethonium carbonate, stearalkonium carbonate, cetrimonium carbonate, behentrimonium carbonate, dioctyldimethylammonium bicarbonate, decyloctyldimethylammonium bicarbonate, didecyldimethylammonium bicarbonate, benzalkonium bicarbonate, benzethonium bicarbonate, stearalkonium bicarbonate, cetrimonium bicarbonate, behentrimonium bicarbonate and mixtures of one or more such carbonate salts. The compositions of the invention may include from 0.2% by weight to 15.0% by weight of one or more carbonate/bicarbonate salts of quaternary ammonium cations.

available from Nalco Company). The compositions in Table 1 also included 0.4% by weight urea; further, the compositions included the indicated type and amount of organic solvent and the remainder of the compositions was water. Note, while an organic solvent was used for purposes of these examples, the solvent is not needed for the compositions of the invention to have the described efficacy and durability. In fact, before the treated surfaces were insulted as described below, the treated surfaces were allowed to dry and the solvent and water would have evaporated. Each of these compositions produced the indicated log reduction of microorganisms within five minutes after twenty-five individual insults of $10^6$ E. coli organisms.

TABLE 1

| Example | Wt. % and type of Solvent | Wt. % of $H_2O_2$ at Time Zero | Wt. % of $H_2O_2$ after 3 Freeze/Thaw Cycles | Wt. % of $H_2O_2$ after 1 Week at 50° C. | Wt. % of $H_2O_2$ after 1 Month at 40° C. | Wt. % of $H_2O_2$ after 3 Months at 25° C. |
|---|---|---|---|---|---|---|
| 1 | 0% Ethanol | 3.15 | 2.94 | 2.92 | 3.07 | Not tested |
| 2 | 2.5% Ethanol | 3.12 | 3.14 | 2.94 | 3.07 | Not tested |
| 3 | 5.0% Ethanol | 3.13 | 3.14 | 2.93 | 3.08 | Not tested |
| 4 | 7.5% Ethanol | 3.10 | 3.10 | 2.92 | 3.04 | Not tested |
| 5 | 5.0% Ethylene Glycol | 3.11 | 3.09 | 2.86 | 3.02 | Not tested |
| 6 | 5.0% Propylene Glycol | 3.10 | 3.10 | 2.85 | 3.02 | 3.10 |
| 7 | 5.0% Butylene Glycol | 3.06 | 3.04 | 2.82 | 2.98 | Not tested |
| 8 | 5.0% Butyl Cellosolve | 3.11 | 3.09 | 2.88 | 3.03 | Not tested |

The compositions of the invention also include an organic acid. Organic acids are also known to have efficacy against the growth of microorganisms. The organic acid may be selected from citric, malic, maleic, oxalic, glutaric, succinic, lactic, glycolic, fumaric, acetic, benzoic, propionic, sorbic, tartaric, formic and mixtures of one or more such organic acids. The compositions of the invention may include from 0.1% by weight to 3.0% by weight of one or more organic acids.

Additionally, the compositions of the invention include hydrogen peroxide. The hydrogen peroxide is stable in the compositions of the invention, despite the presence of the carbonate/bicarbonate salt. Existing antimicrobial compositions do not contain stabilized hydrogen peroxide in combination with a carbonate/bicarbonate salt. The stability of the hydrogen peroxide is measured by the compositions of the invention maintaining their initial concentration and efficacy during shelf-life studies. For example, the compositions remain effective (meaning, they have the same level of durability to effect a log 2 reduction in organisms after twenty-five insults of $10^6$ organisms) after storage for three months at 40° C.; further, the compositions remain effective after storage for one month at 50° C., nine months at 25° C. and after three freeze-thaw cycles. Specifically, the concentration of hydrogen peroxide in exemplary compositions of the invention after various shelf-life studies is provided in Table 1 below. The exemplary compositions in Table 1 each included the following components: (1) 2% by weight of CARBOQUAT H solution as available from Lonza Group Limited Switzerland; (2) 0.85% by weight of citric acid; (3) 3% by weight hydrogen peroxide; and (4) 2.5% by weight polyquaternium-22 polymer (MERQUAT 295 polymer The results in Table 1 show that compositions of the invention are stable as indicated by sustained presence of hydrogen peroxide under different shelf-life study conditions.

While not wishing to be bound by theory, it is believed that the ability to provide compositions with stabilized hydrogen peroxide significantly expands the range of microorganisms that the compositions of the invention are effective against. Some microorganisms exist or are spread in spore form, where the spores have an outer layer; the outer layer presents a barrier to penetration by some conventional antimicrobial compositions. It is believed that the stabilized hydrogen peroxide in the compositions of the invention is capable of penetrating the outer layer of spores, thereby facilitating exposure of the spore interior to the carbonate/bicarbonate salt of a quaternary ammonium cation. The carbonate/bicarbonate salt of a quaternary ammonium cation prevents future germination or development of the spore. The compositions of the invention may include from 0.5% by weight to 5.0% by weight of hydrogen peroxide.

The stability of the compositions of the invention is also measurable by the ongoing/sustained detectable concentration of the carbonate/bicarbonate salt of a quaternary ammonium cation, organic acid and hydrogen peroxide components of the compositions. The carbonate/bicarbonate salt of a quaternary ammonium cation component may be detected using high pressure liquid chromatography (HPLC) with an evaporative light-scattering (ELS) detector. The mobile phase for the HPLC is an acidic mixture of acetonitrile and water. The organic acid component may be detected using HPLC with an ultra-violet (UV) absorption detector monitoring the 220 nanometer wavelength. The mobile phase for the HPLC for the detection of the organic acid is also an acidic mixture of acetonitrile and water. The hydrogen peroxide component may be detected by titrating the sample with a solution of ceric sulfate and ferroin indicator as described in the journal article, Frank P. Greenspan and Donald G. MacKellar entitled "Analysis of Aliphatic Per Acids" published in *Analytical Chemistry*, 1948, 20, 1061. The compositions of the invention have a sustained and detectable presence of these components after experiencing the accelerated shelf-life conditions described herein.

The durability of the hydrogen peroxide in the presence of the carbonate/bicarbonate salt is provided by the polymer component of the compositions of the invention. The polymer is selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, poly(t-butyl acrylate co-ethyl acrylate co-methacrylic acid), polyethylene oxide, polyquaternium-16, polyquaternium-22, polyquaternium-67 and mixtures of such polymers. The compositions of the invention may include from 0.5% by weight to 10% by weight of polymer.

In addition to the components described herein, the compositions of the invention may also include a polar carrier solvent, pH adjuster, fragrance, preservative, dye, corrosion inhibitor, builder, compatible surfactant, cleansing solvent and other components known to be useful in antimicrobial compositions. The compositions of the invention may include from 67% by weight to 98% by weight of one or more of these other components.

While other blending methods may be used, an example of one method of blending the compositions of the invention is as follows: (1) Add water to vessel for mixing of the components of the compositions; (2) Slowly add the carbonate/bicarbonate salt of the quaternary ammonium cation component to the vessel; (3) Slowly add the organic acid component to the vessel and begin mixing at low revolutions per minute (RPM) (i.e. 150-250 RPM); (4) Continue mixing until any foam that is present dissipates (e.g. up to 10 minutes for a 1 liter batch); (5) If desired for additional stability when the final composition is applied to a surface, add a stabilizer such as urea and continue mixing at low RPM (e.g. add 0.4% by weight of urea if adding 3.0% by weight hydrogen peroxide); (6) Slowly add hydrogen peroxide to the vessel and continue mixing at low RPM; (7) Slowly add the polymer component to the vessel and continue mixing at low RPM; (8) If desired for solution clarity, an appropriate organic solvent (e.g. ethanol, isopropanol, ethylene glycol, propylene glycol, butylene glycol, ethylene glycol monobutyl ether, etc.) may slowly be added to the vessel; and (9) If necessary, adjust the pH of the final composition in the vessel to pH 3.0 (+/−0.25) with a dilute (10-25% by weight) solution of potassium hydroxide. Those of skill in the art will appreciate that there are other methods by which the components of the compositions of the invention may be blended. However, it is an aspect of the present invention that the carbonate/bicarbonate salt of the quaternary ammonium cation is neutralized by the addition of the organic acid in step 3 prior to the addition of the hydrogen peroxide.

Representative examples of the polymers of the compositions of the invention are provided in Table 2 below. Each exemplary polymer described in Table 2 was used in a composition of the invention that included the following components: (1) 2% by weight of CARBOQUAT H solution as available from Lonza Group Limited Switzerland; (2) 0.85% by weight of citric acid; and (3) 3% by weight hydrogen peroxide. The compositions also included 0.4% by weight urea and 20% ethanol; the remainder was water. Note, while ethanol was used for purposes of these examples, the ethanol is not needed for the compositions of the invention to have the described efficacy and durability. In fact, before the treated surfaces were insulted as described below, the treated surfaces were allowed to dry and the ethanol and water would have evaporated. Similarly, while not required, the urea is added to provide enhanced stability of the compositions after application to a surface. Each of these compositions produced the indicated log reduction of microorganisms within five minutes after twenty-five and/or fifty individual insults of $10^6$ *E. coli* organisms.

TABLE 2

| Example | Polymer Name | Trade Name or Molecular Weight Range | Supplier | Wt. % polymer | Log Reduction after 25 insults | Log Reduction after 50 insults |
|---|---|---|---|---|---|---|
| 1 | cationic amine polymer-epichlorohydrin adduct | Crepetrol 970 | Ashland | 5.0 | 5.6 | 4.7 |
| 2 | cationic amine polymer-epichlorohydrin resin | Crepetrol X-cell | Ashland | 5.0 | 6.1 | 4.7 |
| 3 | poly(methacrylamidopropyl trimethylammonium) Chloride | MAQUAT PQ-125 | Mason Chemical Company | 2.5 | 6.8 | 6.0 |
| 4 | poly(bis(2-chloroethyl)ether-alt 1,3,bis (dimethylamino)propyl) urea | Polyquaternium-2, Mirapol A-15 | Rhodia | 5.0 | 2.3 | no data |
| 5 | poly(bis(2-chloroethyl)ether-alt 1,3,bis (dimethylamino)propyl) urea | Polyquaternium-2, Mirapol A-15 | Rhodia | 2.5 | 6.6 | 6.0 |
| 6 | poly(diallyldimethyl ammonium chloride | MW 200000-350000 | Sigma-Aldrich | 5.0 | 5.7 | 4.7 |
| 7 | poly(diallyldimethyl ammonium chloride | MW 400000-500000 | Sigma-Aldrich | 2.5 | no data | 6.3 |
| 8 | poly(diallyldimethyl ammonium chloride | MW 400000-500000 | Sigma-Aldrich | 7.5 | no data | 6.0 |
| 9 | poly(t-butyl acrylate co-ethyl acrylate co-methacrylic acid | MW ~100000 | Sigma-Aldrich | 5.0 | 2.5 | no data |
| 10 | polyethylene oxide | MW ~300000 | Sigma-Aldrich | 2.5 | 2.4 | no data |
| 11 | Polyquaternium-16 | Luviquat Excellence | BASF | 5.0 | 4.7 | 2.8 |
| 12 | Polyquaternium-16 | Luviquat Style | BASF | 7.5 | no data | 6.1 |
| 13 | Polyquaternium-16 | Luviquat | BASF | 2.5 | 2.9 | no data |

TABLE 2-continued

| Example | Polymer Name | Trade Name or Molecular Weight Range | Supplier | Wt. % polymer | Log Reduction after 25 insults | Log Reduction after 50 insults |
|---|---|---|---|---|---|---|
| 14 | Polyquaternium-22 | Excellence Merquat 295 | Nalco Company | 2.0 | 6.0 | 4.7 |
| 15 | Polyquaternium-22 | Merquat 295 | Nalco Company | 1.0 | no data | 6.3 |
| 16 | Polyquaternium-22 | Merquat 295 | Nalco Company | 3.0 | no data | 6.3 |
| 17 | Polyquaternium-67 | SoftCAT Polymer SX-400 | Dow Chemical | 5.0 | 2.0 | no data |

The "no data" designations indicate insult conditions that were not tested either because (i) the polymer at a lower wt. % already demonstrated at least a log 3 reduction after twenty-five insults or (ii) the polymer demonstrated close to a log 2 reduction after twenty-five insults and therefore, was unlikely to demonstrate a log 2 reduction after fifty insults.

In addition to the log reduction data for the compositions of the invention provided in Table 2 above, stability data for some of the compositions is provided in Table 3 below. Stability is demonstrated by a continued presence of hydrogen peroxide in the compositions after exposure to different shelf-life conditions. Each of the compositions in Table 3 contained components similar to those described for the compositions of Table 2.

TABLE 3

| Example | Wt. % and type of Polymer | Wt. % of $H_2O_2$ at Time Zero | Wt. % of $H_2O_2$ after 2 Weeks at 50° C. | Wt. % of $H_2O_2$ after 4 Weeks at 50° C. | Wt. % of $H_2O_2$ after 1 Month at 40° C. | Wt. % of $H_2O_2$ after 3 Months at 40° C. |
|---|---|---|---|---|---|---|
| 1 | 2.5% Poly(methyacrylamidopyl-triethyl ammonium) Chloride | 2.99 | 2.99 | 2.88 | 3.03 | 2.90 |
| 2 | 1.0% Polyquaternium-22 | 3.05 | 2.98 | 2.90 | 3.04 | 2.89 |
| 3 | 7.5% Polyquaternium-16 | 2.97 | 2.90 | 2.74 | 2.95 | 2.58 |

The results in Table 3 show that compositions of the invention are stable as indicated by sustained presence of hydrogen peroxide under different shelf-life study conditions.

While the compositions of the invention have been described in detail with respect to specific aspects thereof, it will be appreciated that those skilled in the art, upon attaining an understanding of the foregoing, may readily conceive of alterations to, variations of and equivalents to these compositions. Accordingly, the scope of the present invention should be assessed as that of the claims and any equivalents thereto.

We claim:

1. A composition having durable antimicrobial activity comprising:
   a carbonate/bicarbonate salt of a quaternary ammonium cation;
   an organic acid;
   hydrogen peroxide; and
   a polymer selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, polyquaternium-16, polyquaternium-22, and mixtures thereof,
   wherein the composition is liquid at room temperature,
   wherein the composition comprises from 67% by weight to 98% by weight of a polar carrier solvent, wherein the polar carrier solvent comprises water, and wherein water comprises at least 50% of the composition by weight of the composition, and wherein the composition is stable after storage for three months at 40° C. to retain antimicrobial activity after twenty-five insults of E. coli as measured by a log 3 reduction in organisms upon the twenty-fifth insult of $10^6$ total organisms.

2. The composition of claim 1 wherein the carbonate/bicarbonate salt of a quaternary ammonium cation is selected from dioctyldimethylammonium carbonate, decyloctyldimethylammonium carbonate, didecyldimethylammonium carbonate, benzalkonium carbonate, benzethonium carbonate, stearalkonium carbonate, cetrimonium carbonate, behentrimonium carbonate, dioctyldimethylammonium bicarbonate, decyloctyldimethylammonium bicarbonate, didecyldimethylammonium bicarbonate, benzalkonium bicarbonate, benzethonium bicarbonate, stearalkonium bicarbonate, cetrimonium bicarbonate, behentrimonium bicarbonate and mixtures thereof.

3. The composition of claim 1 wherein the organic acid is selected from citric, malic, maleic, oxalic, glutaric, succinic, lactic, glycolic, fumaric, acetic, benzoic, propionic, sorbic, tartaric, formic and mixtures thereof.

4. The composition of claim 1 wherein the composition further comprises urea.

5. The composition of claim 1 wherein the composition is effective against Gram positive bacteria, Gram negative bacteria, enveloped viruses, non-enveloped viruses, fungi, fungal spores, mildew and mold.

6. The composition of claim 1 wherein the composition includes from 0.2% by weight to 15.0% by weight of the carbonate/bicarbonate salt of a quaternary ammonium cation.

7. The composition of claim 1 wherein the composition includes from 0.1% by weight to 3.0% by weight of the organic acid.

8. The composition of claim 1 wherein the composition includes from 0.5% by weight to 5.0% by weight of hydrogen peroxide.

9. The composition of claim 1 wherein the composition includes from 0.5% by weight to 10% by weight of polymer.

10. The composition of claim 1 wherein the composition is incorporated into a nonwoven basesheet.

11. A nonwoven basesheet including a durable, antibacterial composition comprising from 0.2 to 15.0% by weight of a carbonate/bicarbonate salt of a quaternary ammonium cation;

from 0.1 to 3.0% by weight of an organic acid;
from 0.5 to 5.0% by weight of hydrogen peroxide; and
from 0.5 to 10% by weight of a polymer selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, polyquaternium-16, polyquaternium-22, and mixtures thereof, wherein the composition is liquid at room temperature,
wherein the composition comprises from 67% by weight to 98% by weight of a polar carrier solvent, wherein the polar carrier solvent comprises water, and wherein water comprises at least 50% of the composition by weight of the composition, and wherein the composition is stable after storage for three months at 40° C. to retain antimicrobial activity after twenty-five insults of E. coli as measured by a log 3 reduction in organisms upon the twenty-fifth insult of $10^6$ total organisms.

12. A method of providing sustained antimicrobial activity on a surface comprising the steps of:

providing a composition, the composition comprising a carbonate/bicarbonate salt of a quaternary ammonium cation; an organic acid; hydrogen peroxide; and a polymer selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, and mixtures thereof;

applying the composition to the surface in an amount to substantially cover the surface; and re-applying the composition to the surface after 48 hours,
wherein the composition is liquid at room temperature,
wherein the composition comprises from 67% by weight to 98% by weight of a polar carrier solvent, wherein the polar carrier solvent comprises water, and wherein water comprises at least 50% of the composition by weight of the composition, and wherein the composition is stable after storage for three months at 40° C. to retain antimicrobial activity after twenty-five insults of E. coli as measured by a log 3 reduction in organisms upon the twenty-fifth insult of $10^6$ total organisms.

13. The composition of claim 1, wherein the polymer is selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, polyquaternium-22, and mixtures thereof.

14. The nonwoven basesheet of claim 11, wherein the polymer is selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, polyquaternium-22, and mixtures thereof.

15. The method of claim 12, wherein the polymer is selected from cationic amine polymer-epichlorohydrin adduct, cationic amine polymer-epichlorohydrin resin, poly(methacrylamidopropyltrimethylammonium) chloride, poly(bis(2-chloroethyl)ether-alt-1,3-bis(dimethylamino)propyl)urea, poly(diallyldimethylammonium) chloride, polyquaternium-22, and mixtures thereof.

* * * * *